(12) United States Patent
Thomadsen et al.

(10) Patent No.: US 7,578,781 B2
(45) Date of Patent: Aug. 25, 2009

(54) DEVICE FOR PLACEMENT OF NEEDLES AND RADIOACTIVE SEEDS IN RADIOTHERAPY

(75) Inventors: Bruce R. Thomadsen, Madison, WI (US); Warren D. D'Souza, Baltimore, MD (US); Michael Meltsner, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 699 days.

(21) Appl. No.: 10/944,034

(22) Filed: Sep. 17, 2004

(65) Prior Publication Data

US 2005/0124845 A1 Jun. 9, 2005

Related U.S. Application Data

(60) Provisional application No. 60/504,569, filed on Sep. 18, 2003, provisional application No. 60/572,962, filed on May 20, 2004.

(51) Int. Cl.
*A61M 36/00* (2006.01)

(52) U.S. Cl. ........................................................ 600/7
(58) Field of Classification Search ................. 600/1–8, 600/427, 439; 424/1.11, 1.33; 604/57, 93.01, 604/59, 60, 49, 515; 250/493.1, 497.1
See application file for complete search history.

(56) References Cited

U.S. PATENT DOCUMENTS

| 6,436,068 | B1 | 8/2002 | Bardy |
| 6,482,142 | B1 | 11/2002 | Winkler et al. |
| 6,537,192 | B1 | 3/2003 | Elliott et al. |
| 2001/0053870 | A1* | 12/2001 | Loffler et al. ................ 600/7 |
| 2003/0018232 | A1 | 1/2003 | Elliott et al. |
| 2003/0109769 | A1* | 6/2003 | Lowery et al. ............... 600/7 |
| 2003/0130573 | A1* | 7/2003 | Yu et al. ................... 600/407 |

* cited by examiner

*Primary Examiner*—Charles A Marmor, II
*Assistant Examiner*—Christine D Hopkins
(74) *Attorney, Agent, or Firm*—Boyle Fredrickson, S.C.

(57) ABSTRACT

An automatic stage allows rapid and more precise needle placement for radiation therapy using implantable radioactive seeds.

7 Claims, 7 Drawing Sheets

DEVICE FOR PLACEMENT OF NEEDLES AND RADIOACTIVE SEEDS IN RADIOTHERAPY

CROSS-REFERENCE TO RELATED APPLICATIONS

This application claims the benefit of U. S. Provisional applications 60/504,569 filed Sep. 18, 2003, and U. S. Provisional Application 60/572,962 filed May 20, 2004.

STATEMENT REGARDING FEDERALLY SPONSORED RESEARCH OR DEVELOPMENT

This invention was made with United States government support awarded by the following agencies: DOE DE-FG07-011D14107. The United States has certain rights in this invention.

BACKGROUND OF THE INVENTION

The present invention is a method and apparatus for treating cancer by inserting radioactive seeds into a patient for a possible curative effect. Permanent implant brachytherapy is a radiation treatment technique in which radioactive sources are implanted directly into the tumor and left in place permanently. Typically 50 to 100 small radioactive sources ("seeds") are implanted in or near the tumorous tissue. The seeds may be a radioactive material contained within a biologically inert capsule. The seeds typically have a half-life between 2 and 75 days providing an average energy of emitted photons from approximately 25 keV to 500 keV, with a commercial source strength ranging from approximately 0.2 to several mCi.

The seeds are of a size, e.g., 0.8 millimeters in diameter and 3.5 to 5 millimeters long, so that they may be implanted with hollow needles. The needles have an outer diameter of 1.3 to 1.5 millimeters, are about twenty centimeters long, and have an inner diameter large enough for the seeds to pass. The seeds may be inserted preloaded in the needle along with spacers controlling their separation. With this approach, the loaded needle is inserted into the patient and then withdrawn while the contained seeds are held in place (effectively, ejected) by a stylet (plunger). Alternatively, the seeds may be dropped one at a time through the needle, either by hand or through the assistance of a device such as the Mick Applicator.

The most common application of permanent implants is in treatment for cancer of the prostate. Placement of the seeds for use in treatment of the prostate may be done transperineally, whereby the needle is guided by a plate having predrilled holes at the intersection of a rectilinear grid with 0.5 cm spacing. The depth of insertion of the needle is confirmed by an image obtained with a transrectal ultrasonic image. In this way, seeds may be accurately placed at selected regular grid locations in a volume. U.S. Pat. (WARF No. 960296.99349) describes a planning method for determining the necessary locations of the seeds to produce a particular pattern of radiation dose and is hereby incorporated by reference.

The hole spacing in the guide-plate influences dosage to the cancerous and normal tissue. Improvement in the dose distribution can be achieved by reducing the spacing to less than 0.5 cm. A reduction in the current hole spacing is not amenable to the equipment used or operating room procedures, however.

SUMMARY OF THE INVENTION

The present invention provides an automated stage for supporting a needle used for the implantation of radioactive seeds at an arbitrary location over an area according to computer control.

In one embodiment, the invention places seeds through an automatic sequence involving the partial withdrawing of the needle around a seed at the tip with the seed held stationary by a plunger wire. This technique allows a variable spacing of seeds along a needle track and eliminates the need for spacers. This technique can also be used to place seeds with multiple strengths of radioactivity. In another embodiment, the invention allows rotational control of the seed orientation to permit automatic placement of directionally emitting seeds. In these contexts, the invention also allows a semi-automatic placement of seeds where a computer directly controls the x-y location of the needle, but where the needle is inserted by hand by the physician, the system providing tactile feedback as to when the right depth (z) has been reached.

Specifically then, the present invention provides a needle assembly for implanting radioactive seeds in tissue. The assembly has an implantation needle movable along an insertion axis under the control of a first actuator and a wire fitting within the needle that is independently movable along the insertion axis. Movement of the wire is under the control of a second actuator. An electronic computer executes a stored program to provide signals to the first and second actuators to: (a) actuate the first actuator to position a distal end of the implantation needle at a seed location in the tissue; (b) actuate the second actuator to move a radioactive seed through the implantation needle to the distal end; (c) actuate the first actuator to withdraw the distal end of the implantation needle by at least a length of the radioactive seed while holding a distal end of the wire fixed with respect to tissue; and (d) actuate the second actuator to retract the wire to a proximal end of the implantation needle. These steps (a)-(d) are repeated for each subsequent seed location before removing the implantation needle from the tissue.

Thus, it is one object of at least one embodiment of the invention to allow seeds to be variably spaced along the track of a needle without the need for preloaded spacers or the like such as may be cumbersome and/or promote inflammation of the tissue.

The needle assembly may include a magazine holding radioactive seeds of different strengths and a third actuator for selecting radioactive seeds of different strengths for inserting into the needle. The electronic computer may execute the stored program to select different strength radioactive seeds.

Thus it is another object of at least one embodiment of the invention to provide a needle assembly that may readily adapt to the placement of different types of seeds along a single or multiple needle tracks.

The distal end of the implantation needle may be withdrawn by substantially more than the length of the radioactive seed while holding the distal end of the wire fixed with respect to tissue.

Thus, it is another object of at least one embodiment of the invention to prevent the suction of the withdrawing needle from pulling the radioactive source back along the track.

The wire may have a blunt end and the assembly may further include a second wire with a sharpened distal tip fitting within the needle and movable therealong. The sharpened distal tip of the second wire maybe positioned at a distal tip of the needle before insertion of the implantation needle into tissue and causing the wire to move with the implantation needle during an insertion of the implantation needle into tissue and then to withdraw from the implantation needle upon completion of insertion.

It is thus another object of at least one embodiment of the invention to take advantage of the fact that preloaded needles are not required to allow use of the sharpened wire system described above.

The needle may be manually movable by a physician along an insertion axis through a trajectory guide and have a position sensor providing a signal indicating the position of the implantation needle along the insertion axis. The invention may receive a depth input signal indicating a desired depth of insertion of the implantation needle in tissue and may further have a force actuator communicating with the implantation needle for applying a countervailing force against insertion as a function of needle position and the depth input signal.

Thus it is another object of at least one embodiment of the invention to allow the physician to manually insert the needle (and thus be sensitive to intervening obstructions and the like), while receiving tactile feedback as to the proper depth of insertion.

The force actuator may be an electronically or mechanically controlled brake providing a resistive force.

It is thus another object of at least one embodiment of the invention to provide feedback that mimics resistance of tissue.

Alternatively, the force actuator may be an electric motor providing a non-resistive opposing force.

It is thus another object of at least one embodiment of the invention to permit more complex tactile feedback in which elasticity and other tissue features may be simulated.

The function of the force may be such as to substantially prevent motion of the needle beyond a location corresponding to the location input signal.

It is thus another object of at least one embodiment of the invention to allow manual insertion while still providing a positive stop controllable by machine.

The invention may use an indexing mechanism holding the needle to receive electronic signals to move the needle among a plurality of needle locations over a movement area crossing the insertion axis and the electronic computer may hold values describing a set of needle locations for a radiation treatment plan to move the stage to the needle locations.

It is thus another object of at least one embodiment of the invention to allow routine aspects of needle location to be handled automatically.

The computer may further hold the depth position signals corresponding to the set of needle locations to output a depth position signal to the force actuator at each needle location.

It is thus another object of at least one embodiment of the invention to provide a variable depth control that automatically indexes for different positions of the needle while allowing manual needle insertion.

The stage holding the needle may receive electronic signals to move the stage among a plurality of needle locations over a movement area crossing the insertion axis and to rotate the stage among a plurality of angles about the insertion axis. The computer may hold values describing a set of needle locations and rotational orientations for a radiation treatment plan and execute a stored program to provide the first electronic signals to the indexing mechanism to move the stage to the plurality of needle locations and rotate the stage to the plurality of angles.

Thus it is another object of at least one embodiment of the invention to provide an automatic system suitable for implanting directionally emitting radioactive seeds.

The implantation needle may have a non-circular lumen engaging features of directionally emitting seeds and allowing sliding of the seeds along the lumen without rotation of the seeds within the lumen.

Thus it is another object of at least one embodiment of the invention to provide automatic control over the rotational orientation of the seeds.

The placement of the needles by the device can be coordinated with and guided by ultrasound or magnetic resonance images and/or television triangulation systems.

These particular objects and advantages may apply to only some embodiments falling within the claims and thus do not define the scope of the invention.

DETAILED DESCRIPTION OF THE PREFERRED EMBODIMENT

Figure 1:
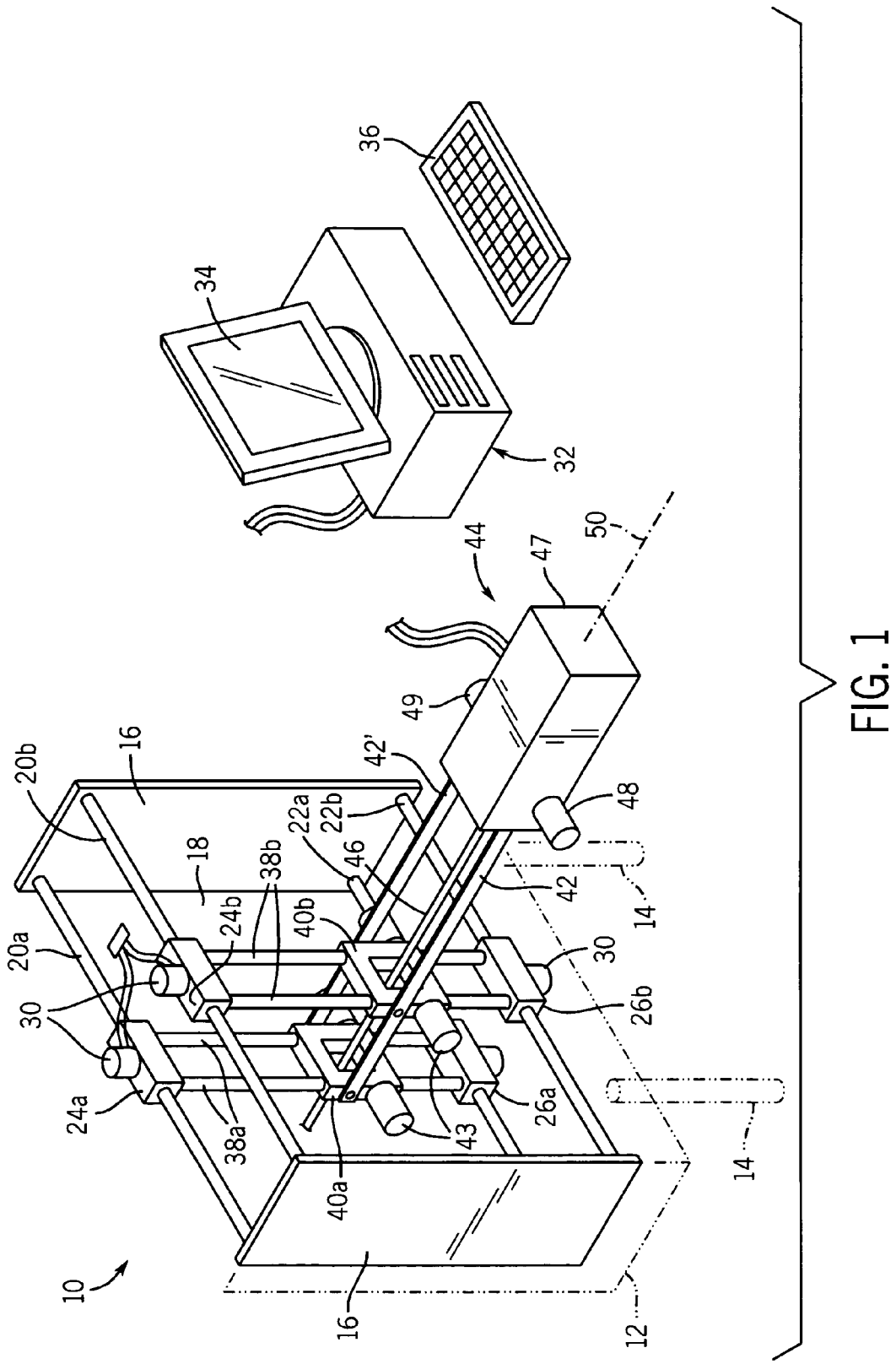
FIG. 1 is a perspective view of the device of the present invention showing an X-Y stage holding a needle assembly and such as communicates with an electronic computer.

Referring now to FIG. 1, a preferred embodiment of the implantation system 10 of the present invention provides an outer framework 12 having downwardly extending guideposts 14 that may be received in a patient table to provide a support fixed with respect to a patient (not shown) on that table.

The outer framework 12 supports vertically extending side panels 16 defining between them a rectangular needle movement area 18 encompassing a range of possible needle locations. The vertically extending side panels 16 are separated by upper front and rear tracks 20a and 20b, respectively, extending perpendicularly from the inner faces of the vertically extending side panels 16 at their upper front and rear edges, respectfully, and lower tracks 22a and 22b extending perpendicularly from the inner faces of the vertically extending side panels 16 at their lower front and rear edge, respectfully.

Each of the tracks 20a and 20b provide ways on which upper carriages 24a and 24b may ride, vertically aligned with lower carriages 26a and 26b on tracks 22a and 22b. Each carriage 24 and 26 holds a servo or stepping motor 30 that may engage a rack cut in an inner side of the tracks 20 and 22 so that movement of the motors 30 propels the carriages 24 and 26 precisely along the tracks 20 and 22. The motors 30 receive electrical signals from a computer 32 or other electronic device controlling their movement. Other mechanisms, including worm gears, lead screws, timing belts and the like may also be used as will be understood to those of ordinary skill in the art.

The computer 32 provides a monitor screen 34 and keyboard 36 and executes a stored program whose function will be described below. In this capacity, it may hold a set of seed locations created by therapy planning software. The computer 32 provides motor drive interface circuitry of a type well known in the art to provide the necessary signals to the motors 30 and other actuators and motors as will be described.

Vertical tracks 38a and 38b, similar to tracks 20 and 22, extend between carriages 24a and 26a, and 24b and 26b, respectively. Tracks 38a support for vertical movement along the tracks 38a, a front stage block 40a, while tracks 38b support for vertical movement along the tracks 38b, a rear stage block 40b. Each of stage blocks 40a and 40b include motors 43 receiving electrical signals from the computer 32 and engaging racks on tracks 38a and 38b to smoothly move the stage blocks 40a and 40b up and down by precise amounts along the tracks 38a and 38b.

Together, the elements described above create an X-Y table allowing arbitrary location of the stage blocks 40a and 40b within parallel planes in the needle movement area 18 according to control by the computer 32. Stage blocks 40a and 40b have central apertures to allow passage of an implantation needle 46 through their centers extending rearward along a needle insertion axis 50 parallel to the side arms 42 into a housing 47.

Stage blocks 40a and 40b support side arms 42 of an implantation needle assembly 44. Side arm 42 attaches to vertical left sides of stage blocks 40a and 40b by pivot points and side arm 42' attaches to vertical right sides of stage block 40a and 40b. A housing 47 supported by rear facing ends of side arms 42 and 42' holds a radioactive seed dispensing mechanism as will be described and supports the rear end of the implantation needle 46.

The implantation needle assembly 44 includes motors 48 allowing the housing to move forward and backwards along the side arms 42 and 42' with respect to the stage blocks 40a and 40b thereby moving the implantation needle 46 along a needle insertion axis 50 into and out of a patient positioned on a front side of the implantation system 10. In this respect, the side arms 42 and 42' may provide ways and racks like tracks 20, 22, and 38.

Figure 2:
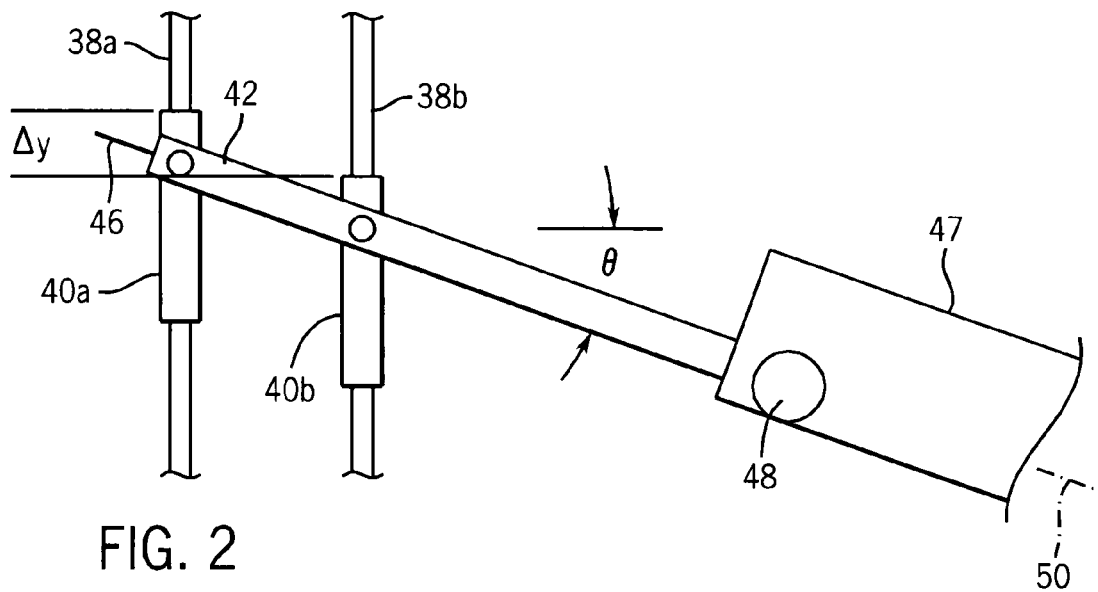
FIG. 2 is a side elevation view of the stage and needle assembly of FIG. 1 with the needle in a retracted position and the stage adjusted for angulation of the needle.
Figure 3:
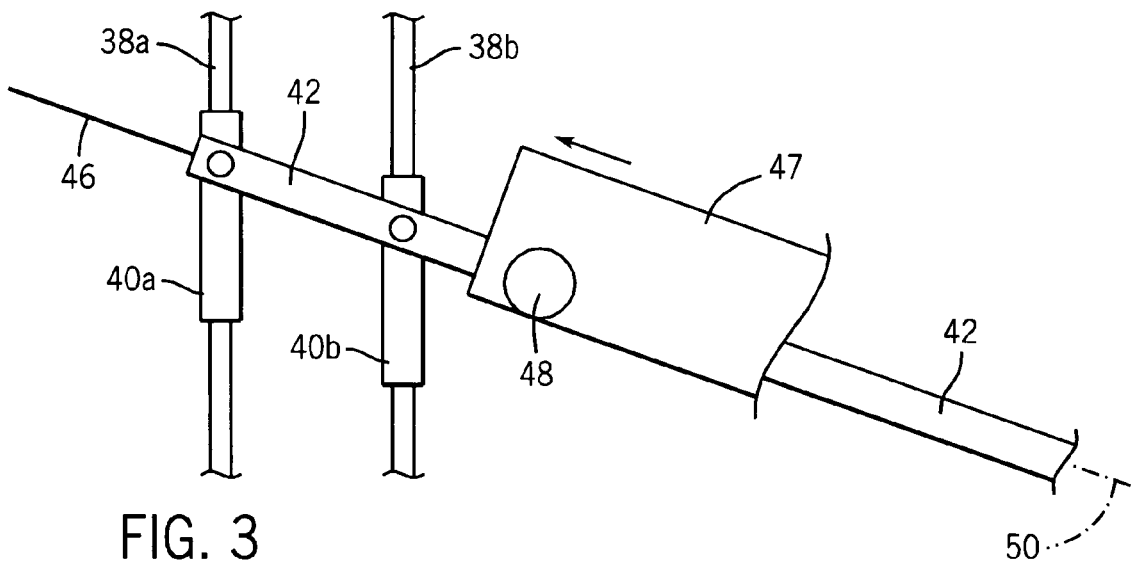
FIG. 3 is a figure similar to that of FIG. 2 showing the needle in an extension position.

Referring to FIG. 2, stage blocks 40a and 40b may be independently adjusted vertically so as to allow an arbitrary vertical angulation of the side arms 42 changing the angle of the needle insertion axis 50 by an amount θ, the value θ being proportional to the difference in height between stage blocks 40a and 40b as may be calculated in computer 32. As shown in FIG. 3, when the housing 47 is drawn along the side arms 42, the needle 46 extends forward along the needle insertion axis 50 at the angle θ.

Referring again to FIG. 1, during placement of radioactive seeds, the computer 32 may sequentially move the stage blocks 40a and 40b to particular locations within the needle movement area 18 and at particular angles as determined by a stored treatment plan. At each location, the needle 46 may be automatically inserted into tissue under control of the computer 32, seeds implanted as will be described, and the needle 46 retracted by the computer 32, and the needle 46 moved to the next needle location. Reproducible precision of less than a millimeter may be easily obtained using standard servo or stepping motor technologies. An attending physician may enter a command on the keyboard 36 between each indexing of the stage blocks 40a and 40b so as to monitor the process and may observe the process using standard ultrasound equipment, such as a rectal ultrasound probe. In addition, the monitor screen 34 may provide an indication of the stage of the completion of the radiotherapy operation to the physician.

Figure 4:
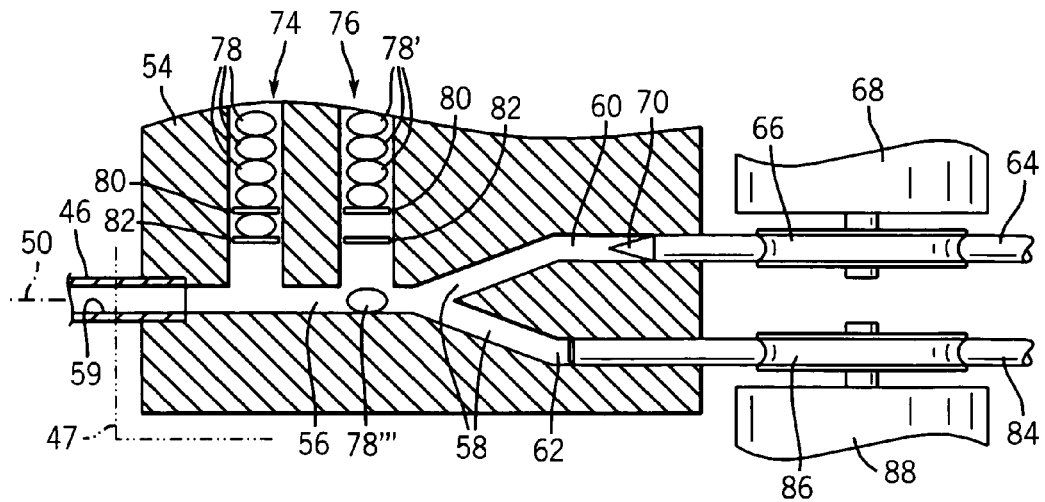
FIG. 4 is a cross-sectional view in elevation of a breech portion of the needle assembly showing actuators for controlling the insertion of a blunt and sharp tipped guide wire through the needle and loading chambers holding radioactive seeds for dispensing them into the path of the blunt wire.

Referring now to FIG. 4 within the housing 47, the needle 46 enters a breech block 54 providing a breech passage 56 extending along the central lumen 59 of the needle 46 to a passage bifurcation 58 leading to an upper bore 60 and a lower bore 62. A flexible wire 64 may be received by upper bore 60 as driven by engaging wheel 66 attached to actuator motor 68. The wire 64 may have a sharpened conical point 70 that may pass forward through the upper bore 60 along the smooth walls of the bifurcation 58 into the breech passage 56 and ultimately into the lumen 59 of the needle 46. The motor 68 is mounted for movement with the housing 47 and so motion of the wire 64 caused by engaging wheel 66 is with respect to the needle 46.

Figure 5:
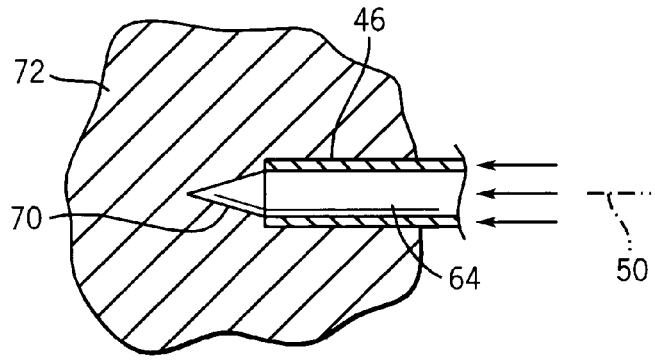
FIG. 5 is a cross-sectional view of a distal end of the needle with the sharp tipped wire fully inserted to provide a tissue-penetrating tip.

Referring now to FIG. 5, during insertion of the needle 46 into tissue 72 of the patient, the sharpened wire 64 is extended by operation of computer 32 so that the sharpened conical point 70 protrudes slightly from the distal portion of the needle 46 to move with the needle 46 as it is inserted into the tissue under the drive of motors 48. The sharpened tip prevents tissue from entering the needle 46 and provides reduced resistance of the needle 46 to entering the tissue while providing a symmetrical surface that does not tend to steer the needle 46 off the needle insertion axis 50.

When the needle 46 is fully inserted, as determined by the most distant location where a radioactive seed should be placed, the wire 64 is wholly retracted by the motor 68 to a position as shown in FIG. 5 also under computer control.

The breech block 54 may include a first and second magazine 74 and 76, each holding a number of radioactive seeds 78 preferably having different radioactive strengths. For example, higher strength seeds 78 may be in magazine 74 and lower strength seeds 78' may be in magazine 76. Alternatively, one of the magazines may hold a fixed length spacer.

The seeds 78 or 78' may be dispensed from either of the magazines 74 and 76 by a feeder mechanism having upper and lower plates 80 and 82 that may be retracted individually by a solenoid under control of the computer 32 to first allow one seed to enter the space between the plates 80 and 82 by momentary retraction of the upper plate 80. A dispensing of the seed 78 or 78' occurs by retraction of the lower plate 82 only.

Once a seed 78 or 78' has been dispensed (as indicated by seed 78"), a blunt wire 84 may be extended into the lower bore 62 by means of wheel 86 driven by motor 88 controlled by the computer 32 to move into the bifurcation 58 and smoothly into the breech passage 56. The motor 88 is also attached to the housing 47 to move with the needle 46.

Figure 6:
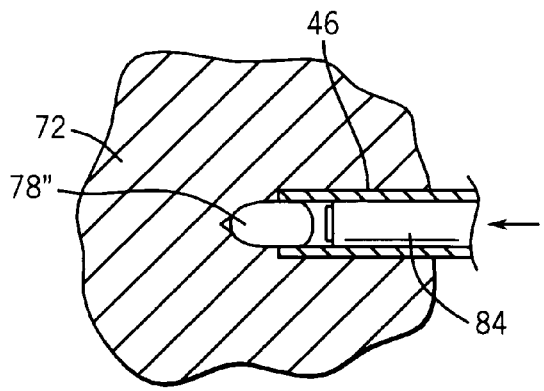
FIG. 6 is a figure similar to that of FIG. 5 showing a retraction of the sharp tipped wire and the use of the blunt tipped wire to push a radioactive seed to the distal end of the needle.
Figure 7:
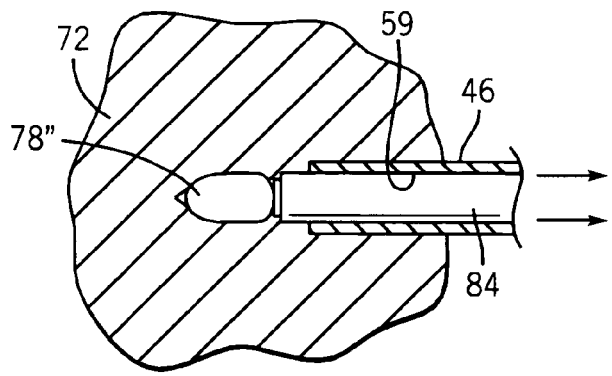
FIG. 7 is a figure showing a retraction of the needle while the blunt wire remains stationary to eject the seed into the tissue.

The front end of the wire 84 is blunt so as to push the seed 78" into the lumen 59 to a distal end of the needle 46 as shown in FIG. 6. The wire 84 stops before the seed 78" is ejected into the tissue and, as shown in FIG. 7, with wire 84 stationary with respect to the tissue 72, the needle 46 is retracted to expose the seed 78" to the tissue and prevent it from being drawn backward by a suction created by the withdrawing needle 46. The wire 84 may provide some clearance with the inner lumen 59 so as to allow a relief of any suction generated when the wire 84 is ultimately retracted. Note that this holding of the wire 84 stationary, with respect to the tissue 72, requires a slight extension of the wire 84 by motor 88 as breech block 54 is retracted under the influence of motor 48 as controlled by the computer 32.

Figure 8:
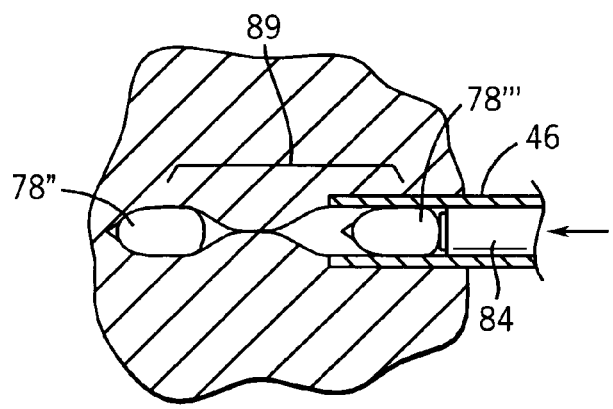
FIG. 8 is a figure similar to that of FIGS. 5 through 7 showing retraction of the needle and blunt wire to a second seed location and preparation for ejection of a second seed.

Referring now to FIG. 8, the needle 46 may be withdrawn an arbitrary distance 89 to a location of a second seed as determined by a treatment plan held in computer 32 without the need for a spacer at which time a second seed 78''' may be dispensed into the breech block 54 and moved to the distal end needle 46 by wire 84 repeating the step shown in FIG. 6.

Once the seeds have been fully placed along a given track, the needle 46 is withdrawn and automatically indexed to a new location by the computer 32. Automation may also reduce the total time necessary for the implantation procedure resulting in less edema developing during the implantation, less trauma, and less expense to the patient.

Figure 9:
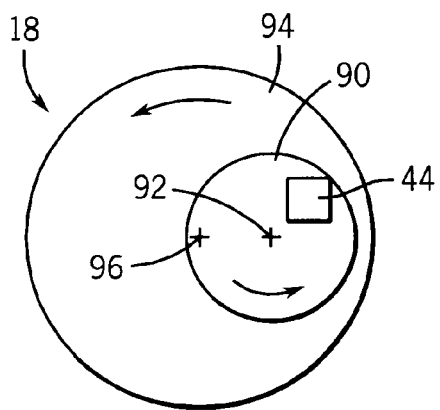
FIG. 9 is a rear elevational view of an alternative mechanism for indexing the needle assembly using rotating platforms.

Referring now briefly to FIG. 9, the X-Y stage shown in FIG. 1 for moving the needle assembly 44 is but one of a number of mechanical solutions to this problem. In a second approach, the needle assembly 44 may be held on a rotating disk 90 having a pivot point 92 about which the disk 90 may be driven by a computer controlled motor allowing rotation of the needle assembly 44 about the pivot point 92. Pivot point 92 may in turn be affixed to a second rotating disk 94 driven by another motor about a pivot point 96. It will be understood that this mechanism will provide movement of the needle assembly 44 throughout a needle movement area 18 that is circular rather than rectangular as shown in the device in FIG. 1, but which in any case, may fully embrace the area over which needles may be desirably placed. It will be understood that more generally the needle movement area need not be planar.

In a simplified embodiment, one or both stage blocks 40*a* and 40*b* may be used to support a sleeve for guiding placement of the needle 46 by a physician who manually inserts the needle 46. In this case a switch, such as a foot switch, may be used to index the stage to the next location, such automatic repositioning still providing a considerable time benefit even with manual needle insertion.

In a variation on this embodiment, the needle 46 can be inserted and removed manually but its position tracked using digital encoders to provide the necessary information to the computer to coordinate movement of the wires as has been described (or the wire mechanism may be physically attached to the needle 46 to move therewith).

Figure 15:
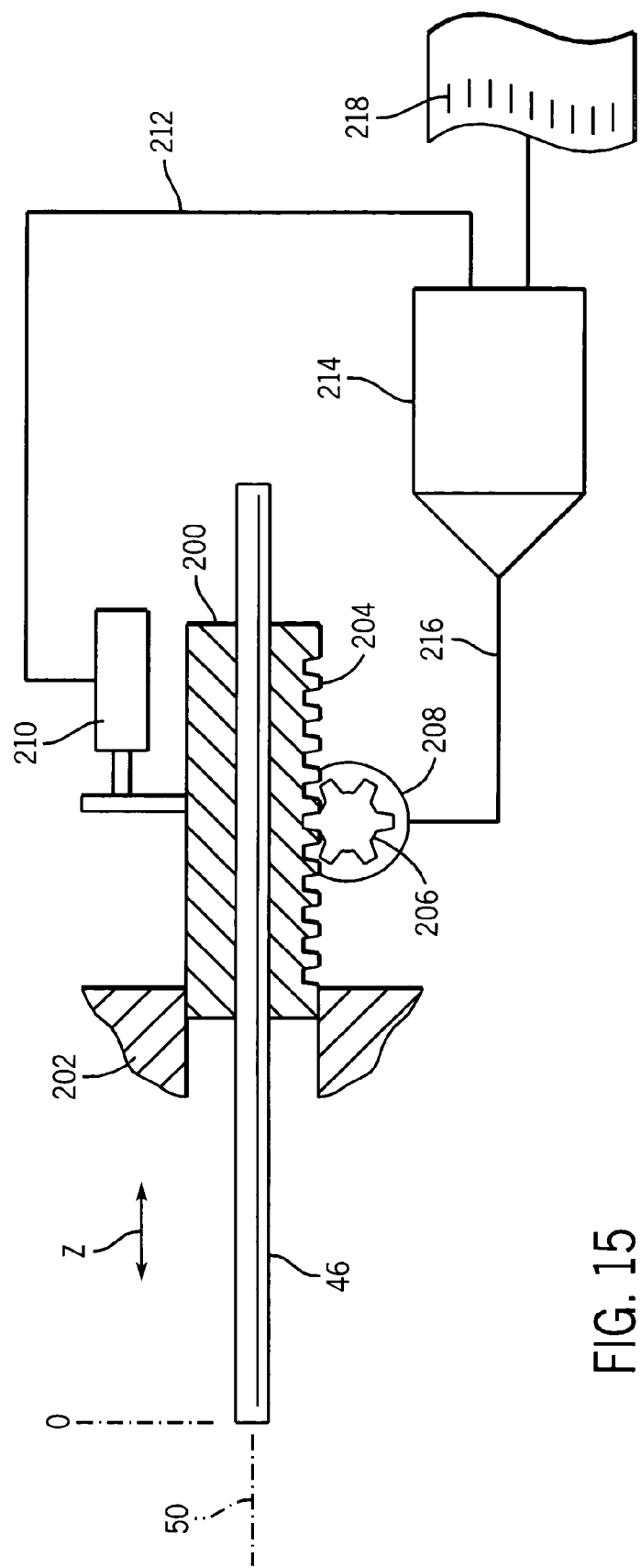
FIG. 15 is a simplified block diagram of a control system for implementing the force function of FIG. 14.

The tracking of the manual insertion of the needle 46 by an encoder may be used to apply a brake or other force feedback to the needle 46 when the correct depth of insertion has been reached. Specifically, referring to FIG. 15 the needle 46 may be held by a slide 200 sliding along the needle insertion axis 50 as held within track 202. A rack 204 on the slide 200 may engage a pinion 206 attached to a force actuator 208 which may, for example, be an electronically controlled clutch or brake or a D.C. motor mounted to be stationary with respect to the patient. The former brake or clutch provide a countervailing force that stops when motion stops, the motor provides a non-resistive force that may be used to cause a minor degree of rebound or elasticity in the movement if desired.

Also attached to the slide 200 is a position encoder 210 providing a needle position signal 212 that may be received by servo function generator 214 to provide a drive signal 216 received by the force actuator 208. The servo function generator 214 may also receive a seed location value 218, being generally a depth component of a three-dimensional coordinate denoting a seed location in an x-y plane and seed depth along a z-axis. The three-dimensional coordinates may be taken directly from a treatment plan and the seed location value 218 may be used to generate a force resisting axial extension of the needle 46 as a function of position of the needle 46 and seed location value 218.

Figure 14:
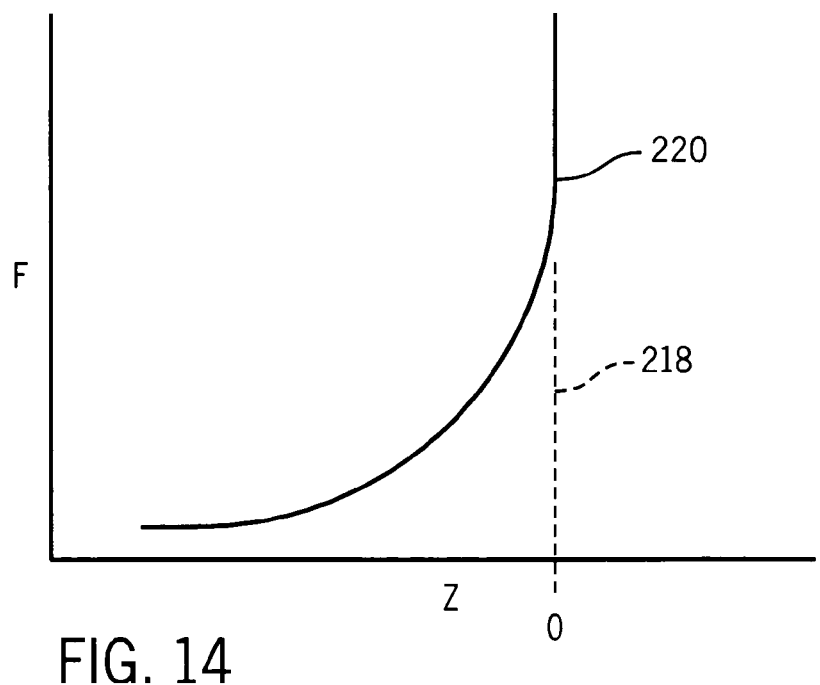
FIG. 14 is a plot of force vs. needle depth as imposed on axial movement of the needle when operated in a manual mode for providing tactile feedback to a physician.

Referring specifically to FIG. 14, the force curve 220 generated by the servo function generator 214 may cause an increasing countervailing force as the needle 46 approaches the depth of the seed location value 218, this force providing tactile feedback to the physician who will feel an increasing resistance force as the depth of the seed location value 218 is approached. On the other hand, prior to reaching the depth of the seed location value 218, the physician will be able to feel and gauge resistance and obstruction to the needle 46 caused by tissue. The force may rise to an arbitrarily high value at the depth of the seed location value 218 so as to stop motion of the needle 46 past this point.

Figure 10:
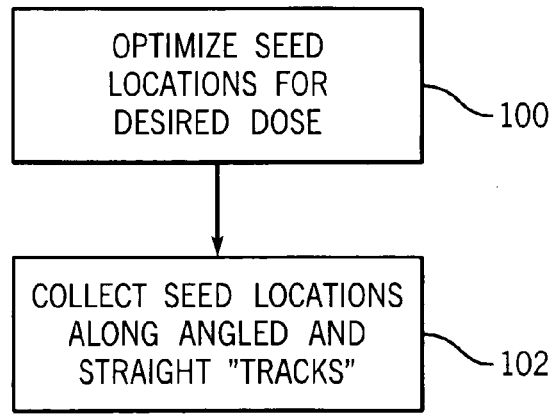
FIG. 10 is a flowchart showing the modification of conventional, brachytherapy planning software for the implementation of non-parallel needle tracts.

It will be understood that the ability to angle the needle insertion axis 50 as described above may be readily extended to vertical and horizontal angulations to increase the flexibility with which the needle is to be placed so as to miss structures that might otherwise block the needle, such as the pelvis. Such angled needle tracks may be readily incorporated into planning software by optimizing seed locations, then collecting the placed seeds into a minimum set of tracks: angled or straight. Thus as shown in FIG. 10, treatment planning as described in the above-referenced patent application, can be done as indicated by process block 102, and then the placed seeds may be collected into a minimum number of needle "tracks" angled or straight. The ability to use angled needle insertion axes 50 may make it possible to reduce a number of needle locations to the extent that a single angled track may intersect seed locations along multiple non-angled needle tracks. The computer 32 may be used to prepare the treatment plan based on previously obtained dose maps as has been described in the co-pending application referenced above or the treatment plan may be prepared on another computer and downloaded to computer 32.

Figure 11:
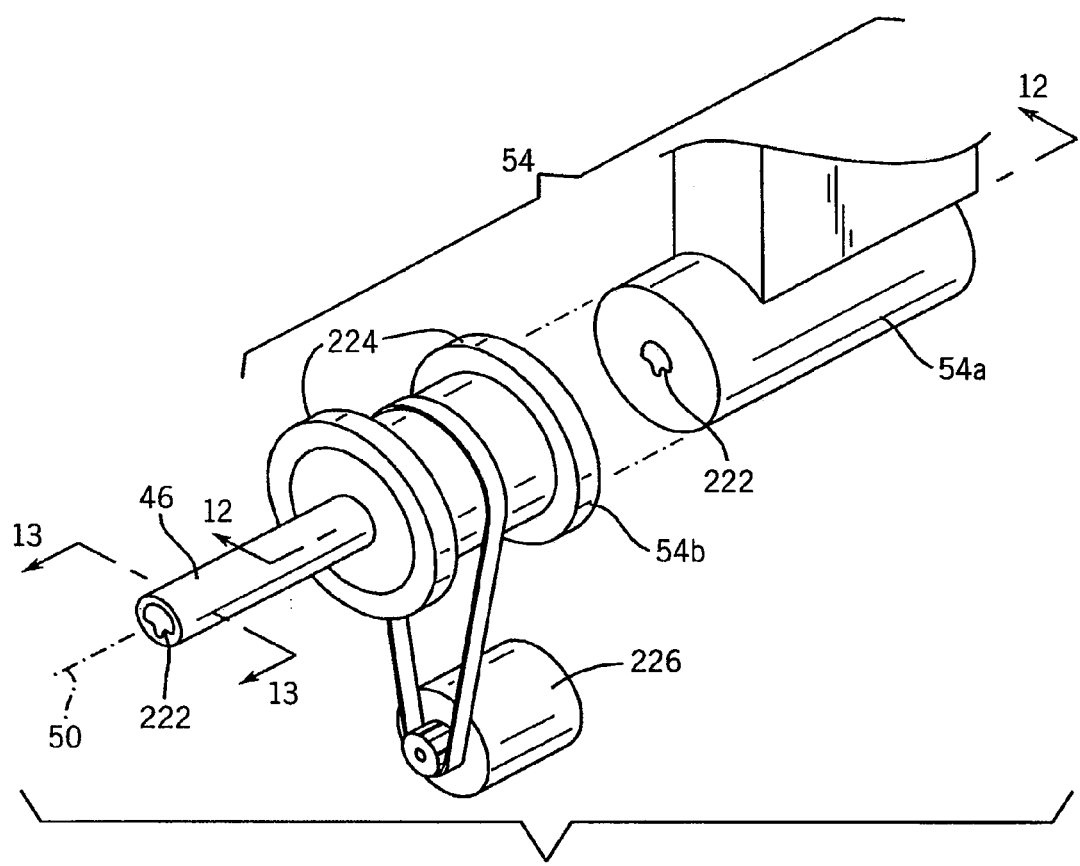
FIG. 11 is an exploded perspective view of an alternative embodiment of the breech block of the needle guide having stationary and rotating portions for controlling rotational orientation of the seeds.
Figure 13:
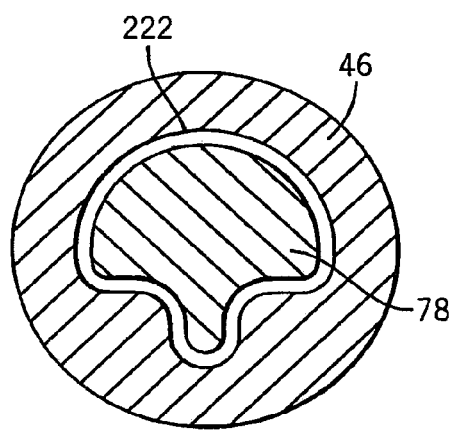
FIG. 13 is a cross-sectional view taken along the lines 13-13 of FIG. 11 showing a conformal lumen orienting a directional seed.
Figure 12:
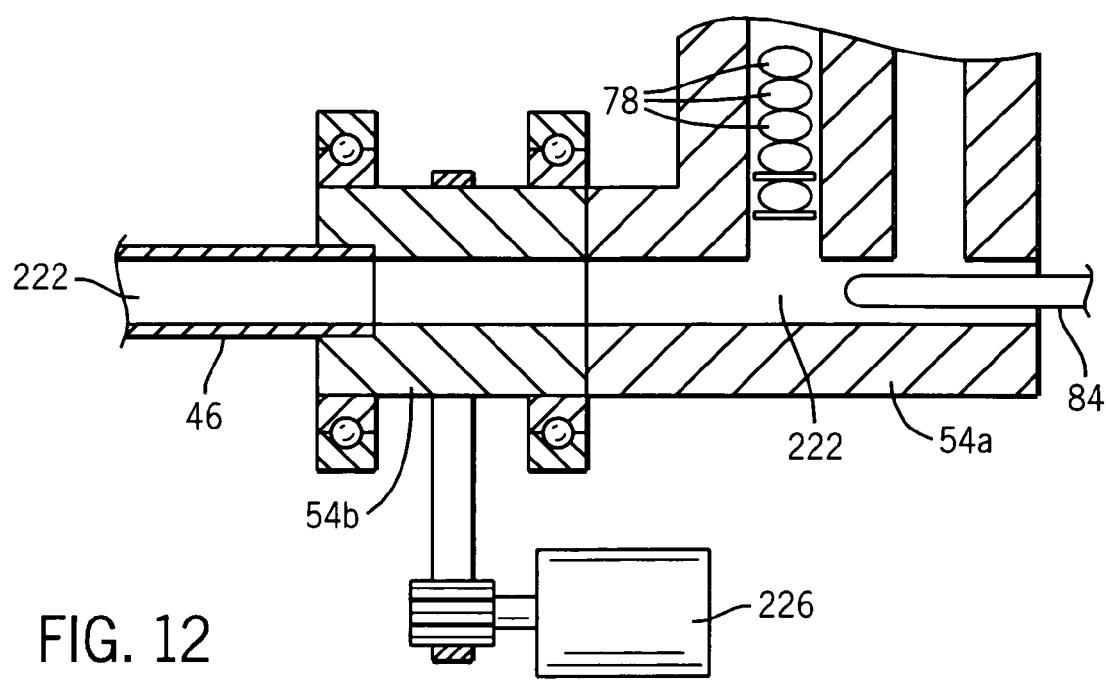
FIG. 12 is a cross-sectional view taken along the lines 12-12 of FIG. 11 showing an interface between the rotating and stationary portions of the breech block.

Referring now to FIGS. 11, 12, and 13, in an alternative embodiment, the apparatus of the present invention may be used with directionally emitting seeds 78. In this embodiment, as shown in FIG. 13, the seeds 78 have a noncircular cross-section (in a plane perpendicular to the needle insertion axis 50) that is held against axial rotation by a conforming lumen 222 of the needle 46. In this case, the breech block 54 is composed of a stationary portion of the breech block 54*a* and a rotating portion of the breech block 54*b*, each portion having identical conforming lumens 222.

The rotating portion of the breech block 54*b* holds the needle 46 and is supported for axial rotation about needle insertion axis 50 by bearings 224 and may be precisely indexed in rotation by a motor 226 such as a servo or stepping motor well-known in the art. When a seed 78 is dispensed into the conformal lumen 222 of the stationary portion of the breech block 54*a*, the rotating portion of the breech block 54*b* is rotated so that its conformal lumen 222 is rotationally aligned with the conformal lumen 222 of the stationary portion of the breech block 54*a*. Wire 84 may then operate to move the dispensed seed 78 into the needle 46 through the rotating portion of the breech block 54*b*.

At this time, the rotating portion of the breech block 54*b* and thus needle 46 may be rotated so as to apply the necessary rotational orientation to directionally emitting seed 78 before it is implanted into tissue.

The use, construction, and treatment planning for such directionally emitting seeds 78 is described in further detail in co-pending U.S. application 60/572,962, filed May 20, 2004, assigned to the same assignee as the present invention and hereby incorporated by reference.

It is specifically intended that the present invention not be limited to the embodiments and illustrations contained herein, but include modified forms of those embodiments including portions of the embodiments and combinations of elements of different embodiments as come within the scope of the following claims. The invention is not limited to use with treatments of the prostate, but may find application in treating other tissues such as the breast, lung, cervix, uterus, bile duct, and other types of tumors. Further the device could also insert empty needles for use with high dose rate or low dose rate temporary implants such as in HDR procedures. In the foregoing, the electronic computer is intended to embrace any circuit producing sequences of control signals according to a stored program or stored firmware.

We claim:

1. A needle assembly for implanting radioactive seeds in tissue comprising:
   an implantation needle movable along an insertion axis under control of a first actuator;
   a wire fitting within the needle and movable therealong independently from movement of the needle along the insertion axis, movement of the wire under the control of a second actuator; and
   an electronic computer executing a stored program to provide signals to the first and second actuators to:
   (a) actuate the first actuator to position a distal end of the implantation needle at a seed location in the tissue;
   (b) actuate the second actuator to move a radioactive seed through the implantation needle to the distal end of the implantation needle;
   (c) actuate the first actuator to withdraw the distal end of the implantation needle by at least a length of the radioactive seed while holding the distal end of the wire fixed with respect to tissue to discharge the seed into tissue;
   (d) actuate the second actuator to retract the wire and implantation needle by a variable spacing between two successive seed locations; and
   (e) repeat steps (b)-(c) at least once for a second seed location before removing the implantation needle from the tissue.

2. The needle assembly of claim 1 further including a magazine holding radioactive seeds of different strengths and a third actuator for selecting radioactive seeds of different strengths for dispensing into the needle;
   wherein the electronic computer executing the stored program selects different strength radioactive seeds for at least two successive cycles of steps (b)-(c).

3. The needle assembly of claim 1 wherein the distal end of the implantation needle is withdrawn by substantially more than the length of the radioactive seed while holding the distal end of the wire fixed with respect to tissue at step (c).

4. The needle assembly of claim 1 wherein the electronic computer executing the stored program varies a linear displacement of the distal end of the needle between successive cycles of steps (a)-(d) to impose a varying spacing to the radioactive seeds.

5. The needle assembly of claim 1 wherein the wire has a blunt end and further including a second wire with a sharpened distal tip fitting within the needle and movable thereal ong;
   wherein the electronic computer executes the stored program to position the sharpened distal tip of the second wire at a distal tip of the needle before insertion of the implantation needle into tissue and causing the wire to move with the implantation needle during an insertion of the implantation needle into tissue and then to withdraw from the implantation needle upon completion of insertion.

6. The needle assembly of claim 1 further including a third actuator for rotating the implantation needle about the insertion axis and wherein the electronic computer executes the stored program to rotate the implantation needle to predetermined angles about the rotation axis in between seed locations.

7. A device for implanting radioactive seeds with a non-circular cross section in tissue comprising:
   an implantation needle extendable along an insertion axis into tissue, the needle further comprising a circular outer diameter and a lumen with a non-circular cross section wherein the circular outer diameter and non-circular lumen extend along substantially an entire length of the needle and the non-circular lumen engages an outer surface of the non-circular seeds to substantially prevent rotation of the seeds along at least a substantial length of the lumen while allowing the seeds to slide within the lumen;
   a stage for supporting the implantation needle;
   an indexing mechanism receiving electronic signals to rotate the implantation needle among a plurality of rotational alignments about the insertion axis wherein the needle remains substantially coaxial with the insertion axis along which it is extended; and
   an electronic computer holding values describing a set of needle locations and rotational orientations for a radiation treatment plan and executing a stored program to provide the electronic signals to move the stage to the plurality of needle locations and to rotate the implantation needle to the plurality of rotational alignments wherein the needle may be rotated to a different rotational orientation either prior to or after insertion into tissue.

* * * * *